United States Patent
Choi et al.

(10) Patent No.: US 10,441,492 B2
(45) Date of Patent: Oct. 15, 2019

(54) POWER TRANSMISSION APPARATUS HAVING TWO BELTS

(71) Applicant: KOREA INSTITUTE OF SCIENCE AND TECHNOLOGY, Seoul (KR)

(72) Inventors: Junho Choi, Seoul (KR); Seung-Jong Kim, Seoul (KR); Jaehwan Park, Seoul (KR); Seunghan Park, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 384 days.

(21) Appl. No.: 15/348,341

(22) Filed: Nov. 10, 2016

(65) Prior Publication Data
US 2018/0008501 A1  Jan. 11, 2018

(30) Foreign Application Priority Data
Jul. 5, 2016 (KR) .................. 10-2016-0084763

(51) Int. Cl.
*A61H 3/00* (2006.01)
*A61H 1/02* (2006.01)
*F16H 7/02* (2006.01)
*F16H 19/00* (2006.01)
(Continued)

(52) U.S. Cl.
CPC ............ *A61H 3/00* (2013.01); *A61H 1/0262* (2013.01); *F16H 7/02* (2013.01); *F16H 19/005* (2013.01); *A61F 2/605* (2013.01); *A61F 2/64* (2013.01); *A61H 1/024* (2013.01); *A61H 1/0244* (2013.01); *A61H 2201/1215* (2013.01); *A61H 2201/14* (2013.01); *A61H 2201/164* (2013.01); *A61H 2201/165* (2013.01); *A61H 2205/10* (2013.01)

(58) Field of Classification Search
CPC ....................................................... A61H 3/00
See application file for complete search history.

(56) References Cited

U.S. PATENT DOCUMENTS

| 5,046,375 A | 9/1991 | Salisbury, Jr. et al. |
| 9,145,955 B2 | 9/2015 | Ferlay et al. |

(Continued)

FOREIGN PATENT DOCUMENTS

| JP | 2007-89634 A | 4/2007 |
| JP | 2014/73222 A | 4/2014 |
| KR | 10-0612031 B1 | 8/2006 |

(Continued)

OTHER PUBLICATIONS

Park, Hae-Won, et al. "Identification of a Bipedal Robot with a Compliant Drivetrain." IEEE Control Systems Magazine 31.2 (Apr. 2011): 63-88. (26 pages in English).

*Primary Examiner* — Matthew W Schall
(74) *Attorney, Agent, or Firm* — NSIP Law (57) ABSTRACT

A power transmission apparatus includes a driving joint unit having a first driving gear fixed to a first driving shaft and a second driving gear fixed to a second driving shaft, an operating joint unit fixed on an operating shaft and having an operating gear rotating together with the operating shaft, a first operating belt connected to the first driving gear and the operating gear, a second operating belt connected to the second driving gear and the operating gear to apply a torque in opposite directions, a driving link having one end connected to the first driving shaft or the second driving shaft and the other end connected to the operating shaft, and an operating link fixed to the operating shaft.

11 Claims, 9 Drawing Sheets

(51) Int. Cl.
　　　*A61F 2/60*　　　　(2006.01)
　　　*A61F 2/64*　　　　(2006.01)

(56) References Cited

U.S. PATENT DOCUMENTS

2014/0100492 A1　4/2014　Nagasaka
2015/0272764 A1　10/2015　Kim et al.

FOREIGN PATENT DOCUMENTS

POWER TRANSMISSION APPARATUS HAVING TWO BELTS

CROSS-REFERENCE TO RELATED APPLICATION

This application claims priority to Korean Patent Application No. 10-2016-0084763, filed on Jul. 5, 2016, and all the benefits accruing therefrom under 35 U.S.C. § 119, the contents of which in its entirety are herein incorporated by reference.

BACKGROUND

1. Field

The present disclosure relates to a power transmission apparatus, and more particularly, to a power transmission apparatus capable of combining and transmitting torques of motors in various ways by using two belts.

2. Description of the Related Art

Various robots implementing motions of a human skeleton and joints are being developed. For example, a humanoid having a shape similar to a human body or a production robot such as a robot arm installed at a production line of a factory actively adopts structural features of the human.

Meanwhile, various walk assist robots for helping a disabled person or a stroke survivor, who has weakened muscular strength and reduced mobility, to walk are being developed. The walk assist robot is a structure implementing motions of a skeleton and joints of the human, required for walking, and the walk assist robot is mounted to a lagging leg to substitute for or assist with motions of each joint and skeleton.

Among components of the walk assist robot, a skeleton and joint may be implemented using a link and a joint. However, the muscle for moving the skeleton and joint is substituted with a motor, a pneumatic or hydraulic actuator or the like.

At this time, for example, if a motor is mounted to each joint to operate each skeleton, the joint at which the motor is mounted should be moved using another motor, and the torque demanded for each joint should be transmitted using a single motor. For this reason, each motor is demanded to give a high torque. Therefore, in order to give a high torque, a high-performance motor having a larger and heavier design is used, which is inefficient in view of energy consumption. In particular, when actuators are mounted to a terminal of a human body, a great load is applied to an actuator located near the center of the human body, resulting in relatively instable motion of a robot.

Therefore, it is demanded to develop a skeleton robot which may be located at a center of a human body and move a skeleton at a terminal with a small force.

SUMMARY

The present disclosure is directed to providing a power transmission apparatus, which applies torques to two driving shafts disposed on a straight line so that one driving shaft is connected to an operating belt to transmit a torque to an operating shaft in the same direction and the other driving shaft is connected to the operating belt to transmit a torque to the operating shaft in opposite directions, thereby implementing various motions of a driving link connected to the operating shaft and the driving shaft and an operating link connected to the operating shaft.

In one aspect of the present disclosure, there is provided a power transmission apparatus, comprising: a driving joint unit having a first driving gear fixed to a first driving shaft and a second driving gear fixed to a second driving shaft and disposed on a straight line together with the first driving shaft; an operating joint unit fixed on an operating shaft and having an operating gear rotating together with the operating shaft; a first operating belt connected to the first driving gear and the operating gear to apply a torque to the first driving gear and the operating gear in the same direction; a second operating belt connected to the second driving gear and the operating gear to apply a torque to the second driving gear and the operating gear in opposite directions; a driving link having one end connected to the first driving shaft or the second driving shaft to be freely rotatable thereon and the other end connected to the operating shaft to be freely rotatable thereon; and an operating link fixed to the operating shaft.

According to an embodiment of the present disclosure, the power transmission apparatus may further include a first motor for transmitting a torque to the first driving shaft and a second motor for transmitting a torque to the second driving shaft, wherein the torque demanded by the first motor may be determined according to a sum of a torque demanded by the driving joint unit and a torque demanded by the operating joint unit, and wherein the torque demanded by the second motor may be determined according to a difference of a torque demanded by the driving joint unit and a torque demanded by the operating joint unit.

According to an embodiment of the present disclosure, the driving joint unit may be fixed to an upper body of a user, the driving link may be fixed to the thigh of the user, the operating link may be fixed to the calf of the user, and the driving link and the operating link may rotate with respect to each other to assist with walking of the user.

According to an embodiment of the present disclosure, the first motor and the second motor may be respectively connected to the first driving shaft and the second driving shaft at a side opposite to a human body of the user.

According to an embodiment of the present disclosure, the driving shafts may be disposed at a side of the hip joint of the user, and the operating shaft may be disposed at a side of the knee joint of the user.

According to an embodiment of the present disclosure, a rotation angle of the thigh with respect to the hip joint of the user may be determined according to a sum of a rotation angle by the first motor and a rotation angle by the second motor, and a rotation angle of the calf with respect to the knee joint of the user may be determined according to a difference of a rotation angle by the first motor and a rotation angle by the second motor.

According to an embodiment of the present disclosure, the second operating belt may be connected to the second driving gear and the operating gear to intersect the same in a figure eight shape.

According to an embodiment of the present disclosure, the first operating belt and the second operating belt may be made of elastic material.

DETAILED DESCRIPTION

Advantages and features of the present disclosure and their solutions will be more apparent from the following detailed description and embodiments taken in conjunction with the accompanying drawings. However, the present disclosure is not limited to the embodiments disclosed below but may be implemented in various ways, and the embodiments are just for more perfect disclosure and better understanding to those having ordinary skilled in the art. The present disclosure is defined just by the scope of the appended claims.

Shapes, sizes, ratios, angles, numbers or the like depicted in the drawings to explain an embodiment of the present disclosure are just for illustrations, and the present disclosure is not limited thereto. In addition, in the description, details of well-known features and techniques may be omitted to avoid unnecessarily obscuring the presented embodiments. When the terms "comprises" and/or "comprising", or "includes" and/or "including" are used in this specification, this means any other component can also be added, unless stated otherwise. As used herein, the singular forms "a", "an" and "the" are intended to include the plural forms as well, unless the context clearly indicates otherwise.

When interpreting a component, it should be understood as including an error range, even though there is no explicit statement.

In case of location-related explanation, for example if a location relation of two components is explained using the terms "on", "above", "below", "beside" or the like, at least one other component may be further located between two components, unless any restrictive term such as 'instantly' or 'directly' is used.

When an electrode or layer is explained as being located "on" another element or layer, this includes all cases where another layer or element is interposed therebetween. Throughout the specification, like reference numerals denote like elements.

Though the terms "first" and "second" are used for explaining various components, these components are not limited thereto. These terms are just used for distinguishing any component from another. Therefore, any "first component" recited below may also be regarded as a second component within the scope of the present disclosure.

The size and thickness of each component in the drawings are just for convenient explanation, and the present disclosure is not limited to the depicted size and thickness.

Features of various embodiments of the present disclosure may be united or combined with each other partially or entirely. As fully understood by those skilled in the art, such features may be technically linked or operated together in various ways, and various embodiments may be implemented independently or together in an associated way.

Hereinafter, a power transmission apparatus according to an embodiment of the present disclosure will be described with reference to the drawings.

Referring to FIGS. 1 to 5, a power transmission apparatus 100 according to an embodiment of the present disclosure includes a driving joint unit 110, an operating belt 120, an operating joint unit 130, a driving link 140, and an operating link 150.

In this embodiment, the power transmission apparatus 100 is a walk assist device and is mounted to one leg 10 of a user to assist the user in walking. Each component of the power transmission apparatus 100 assists a function of each skeleton or joint of the leg, as described later in detail.

A driving joint unit 110 is fixed to an upper body of the user, for example the abdomen, the waist or the like, and assists a role of a hip joint of the user.

The driving joint unit 110 includes a first driving shaft 111a and a second driving shaft 111b whose rotation axis is substantially parallel to the ground and oriented to a side of the user. The first driving shaft 111a and the second driving shaft 111b are disposed on a straight line. In addition, the driving shafts 111a, 111b may be disposed at a side of the hip joint of the user. At this time, the driving joint unit 110 may be firmly fixed to the body of the user so that axial directions of the driving shafts 111a, 111b may be maintained consistently. In particular, the driving joint unit 110 should be firmly fixed to an upper side of the thigh of the user so as to move the thigh with respect to the upper body of the user when the driving link 140 rotates.

The first driving shaft 111a receives a power from a first motor 113a through a first driving belt 112a. In addition, the second driving shaft 111b receives a power from a second motor 113b through a second driving belt 112b. The first driving shaft 111a and the second driving shaft 111b are located on the same straight line but may freely rotate with respect to each other with power individually received from the first motor 113a and the second motor 113b, and their motions do not give a direct influence to each other. For example, when the first motor 113a and the second motor 113b are driven in opposite directions, the first driving shaft 111a and the second driving shaft 111b may rotate in opposite directions.

Meanwhile, the first driving belt 112a and the second driving belt 112b may be disposed separately at both sides of the first driving shaft 111a and the second driving shaft 111b. However, the first driving belt 112a and the second driving belt 112b may also be disposed together at a side opposite to a human body so that the links 140, 150 are closely adhered to the human body as shown in the figures, considering that the rotating forces of the links 140, 150 may be more stably transmitted to the human body in walking when the power transmission apparatus 100 is fixed closer to the human body. In other words, the first motor 113a and the second motor 113b may be connected respectively to the first driving shaft 111a and the second driving shaft 111b at one side opposite to the human body of the user. At this time, the first driving belt 112a and the second driving belt 112b are spaced apart from each other as much as a suitable interval not to overlap with each other.

A first driving gear 114a is fixed to the first driving shaft 111a, and when the first driving shaft 111a rotates, the first driving gear 114a rotates together with the first driving shaft 111a. In addition, a second driving gear 114b is fixed to the second driving shaft 111b, and when the second driving shaft 111b rotates, the second driving gear 114b rotates together with the second driving shaft 111b.

The operating joint unit 130 is disposed near the knee and assists a role of the knee joint of the user.

The operating joint unit 130 includes an operating shaft 131 substantially parallel to the ground and oriented toward a side of the user. The operating shaft 131 may be disposed at a side of the knee joint of the user. The operating shaft 131 may be disposed in parallel to the first driving shaft 111a and the second driving shaft 111b.

An operating gear 134 is fixed to the operating shaft 131. Therefore, when the operating gear 134 rotates, the operating shaft 131 also rotates.

The first driving gear 114a and the operating gear 134 are connected by means of a first operating belt 120a. In addition, the second driving gear 114b and the operating gear 134 are connected by means of a second operating belt 120b. In other words, two operating belts 120a, 120b are connected to a single operating gear 134. At this time, the operating gear 134 may be a single gear having two regions respectively coupled to the operating belts 120a, 120b, or two gears may be secured or integrally formed therefor.

The operating gear 134 is coupled to the first operating belt 120a to rotate in the same direction as a rotation direction of the first driving gear 114a when the first driving gear 114a rotates. In other words, the first operating belt 120a is connected to the first driving gear 114a and the operating gear 134 to apply a torque to the first driving gear 114a and the operating gear 134 in the same direction.

The operating gear 134 is coupled to the second operating belt 120b to rotate in opposite directions as a rotation direction of the second driving gear 114b when the second driving gear 114b rotates. In other words, the second operating belt 120b is connected to the second driving gear 114b and the operating gear 134 to give a torque to the second driving gear 114b and the operating gear 134 in opposite directions. For example, the second operating belt 120b may be coupled to the second driving gear 114b and the operating gear 134 to intersect the same in a FIG. 8 shape as shown in the figures. At this time, when the second driving gear 114b rotates in a clockwise direction, the second operating belt 120b rotates the operating gear 134 in a counterclockwise direction.

Meanwhile, rotation directions of the first operating belt 120a and the second operating belt 120b are not limited to the above, but other configurations may also be available as long as the operating belts are fixed to the shafts respectively so that the rotation directions are identical at one ends of the operating belts and the rotation directions are different at the other ends.

As described above, though torques are applied to first driving shaft 111a and the second driving shaft 111b in the same direction, torques are transmitted to the operating shaft 131 in different directions due to the first operating belt 120a and the second operating belt 120b. Motions of the links 140, 150 caused by this configuration will be described later in detail.

The driving link 140 is fixed to the thigh by means of a fixture 21. Therefore, if the driving link 140 moves, the thigh also moves together.

One end of the driving link 140 is connected to the first driving shaft 111a and the second driving shaft 111b to be freely rotatable thereat. It would be enough if the driving link 140 is freely rotatable on the rotation axes of the driving shafts 111a, 111b with respect to the first driving shaft 111a and the second driving shaft 111b, and the driving link 140 may be connected to any one of the first driving shaft 111a and the second driving shaft 111b. In addition, the other end of the driving link 140 is connected to be operating shaft 131 to be rotatable thereat. By doing so, the first driving shaft 111a and the second driving shaft 111b are spaced apart from the operating shaft 131 by means of the driving link 140.

Meanwhile, the driving link 140 is not limited to the shape depicted in the figures and may be formed to surround the operating belts 120a, 120b so that the operating belts 120a, 120b are not exposed out.

The operating link 150 is fixed to the calf by means of another fixture 22. Therefore, when the operating link 150 moves, the calf also moves together.

The operating link 150 is fixed to the operating shaft 131, and when the operating shaft 131 rotates, the operating link 150 also rotates together.

The power transmission apparatus 100 according to an embodiment of the present disclosure configured as above may rotate the driving link 140 and the operating link 150 in various patterns depending on a driving direction, a torque and a rotation speed of the first motor 113a and the second motor 113b. Hereinafter, this will be described in more detail.

First, according to the driving directions of the first motor 113a and the second motor 113b, the links 140, 150 give different motions When the first motor 113a and the second motor 113b rotate in the same direction, the first driving gear 114a and the second driving gear 114b also rotate in the same direction. Since the rotation directions are changed differently by the first operating belt 120a and the second operating belt 120b, torques are transmitted to the operating gear 134 in opposite directions. Therefore, the operating shaft 131 and the operating link 150 do not rotate with respect to the rotation axis of the operating shaft 131. The sum of the torques respectively transmitted to the motors 113a, 113b with respect to the operating joint unit 130, namely the torque with respect to the rotation axis of the operating shaft 131, becomes 0 (zero).

Meanwhile, the torques respectively transmitted from the motors 113a, 113b are applied in the same direction on the first driving shaft 111a and the second driving shaft 111b. Since the first driving shaft 111a and the second driving shaft 111b are disposed on the same straight line and the torques are applied to the first driving gear 114a and the second driving gear 114b in the same direction, the sum of the torques with respect to the driving joint unit 110, namely the torques with respect to the rotation axes of the driving shafts 111a, 111b, is not 0 (zero).

At this time, since the operating shaft 131 does not rotate and the operating belts 120a, 120b are also fixed without rotating, the operating belts 120a, 120b play a role of rotating arms which move the driving link 140 and the operating link 150 based on the rotation axes of the driving shafts 111a, 111b.

Figure 1:
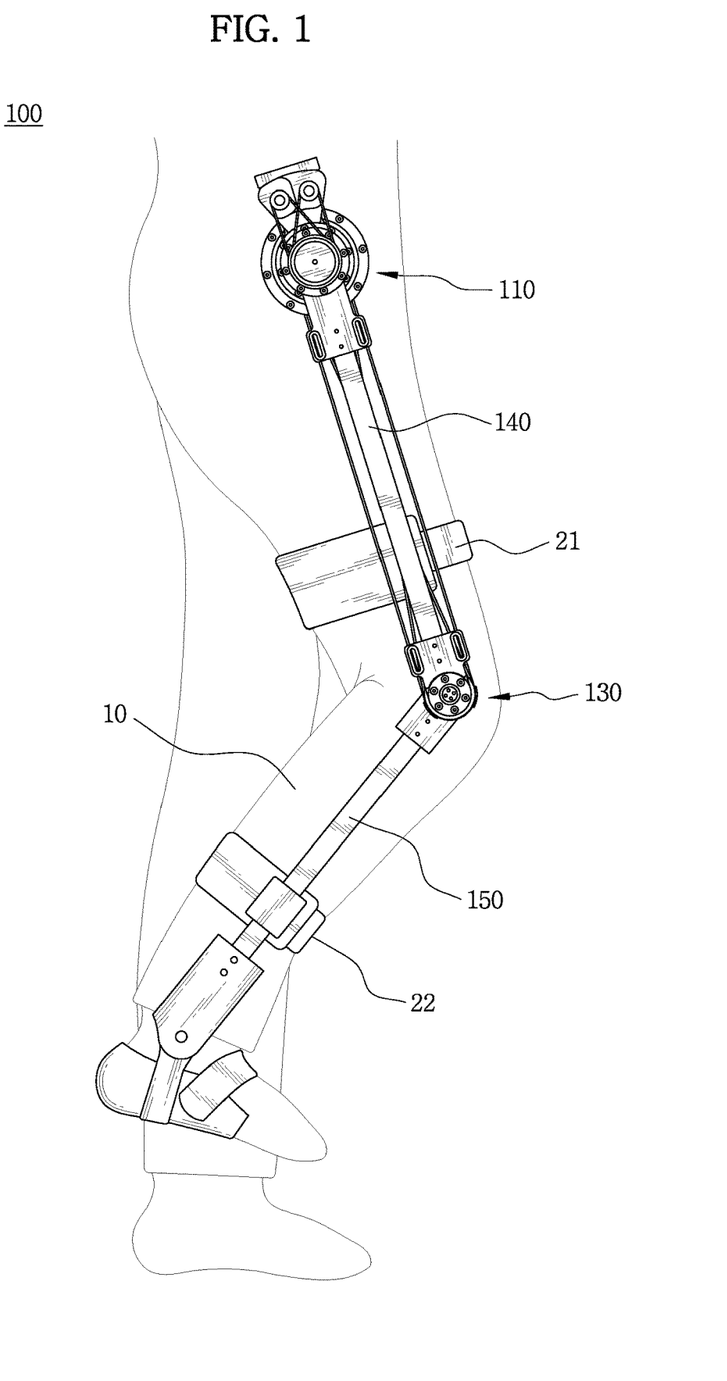
FIG. 1 is a side view showing a power transmission apparatus according to an embodiment of the present disclosure, which is applied to a human body of a user.
Figure 2:
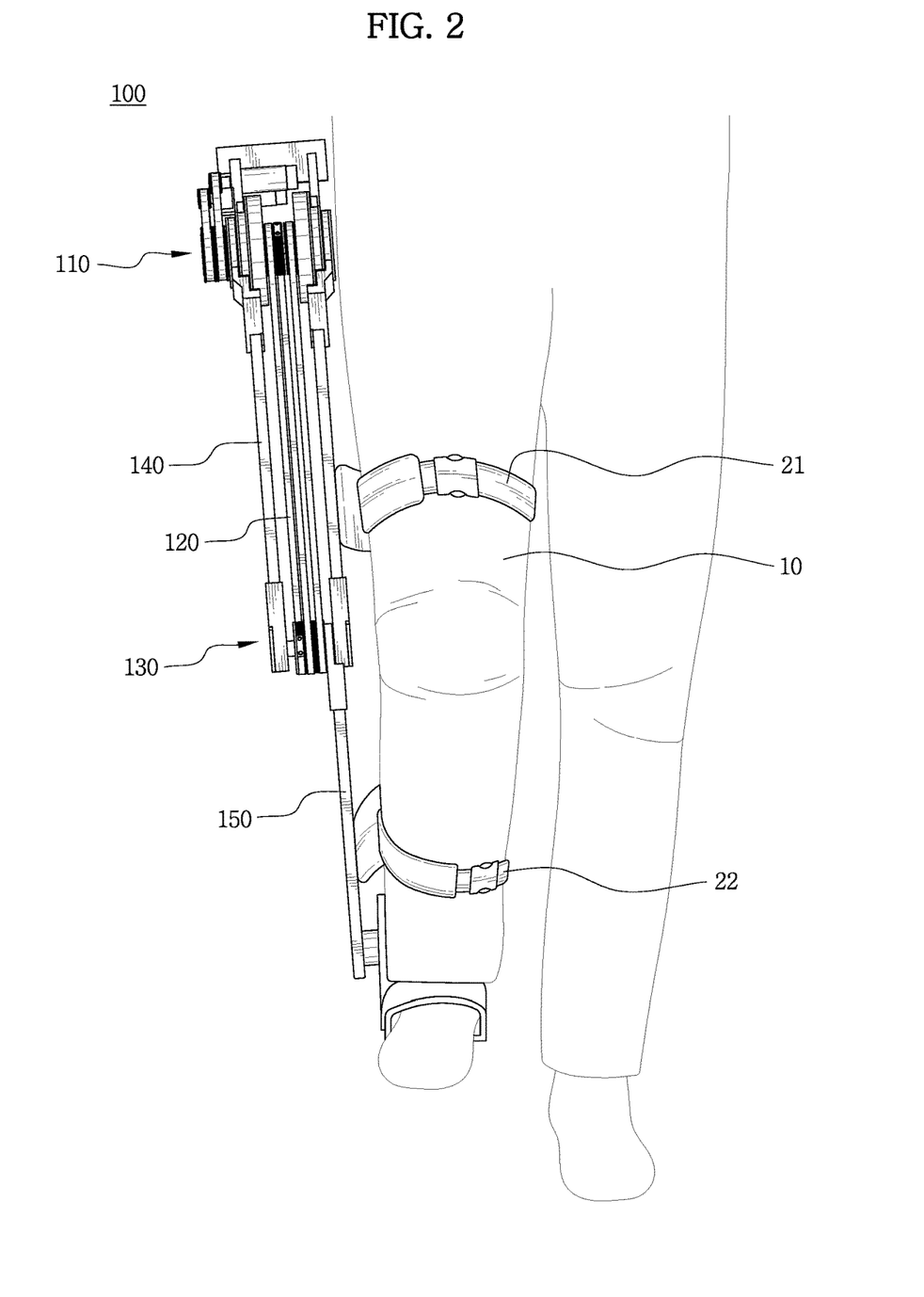
FIG. 2 is a front view showing the power transmission apparatus of FIG. 1.
Figure 3:
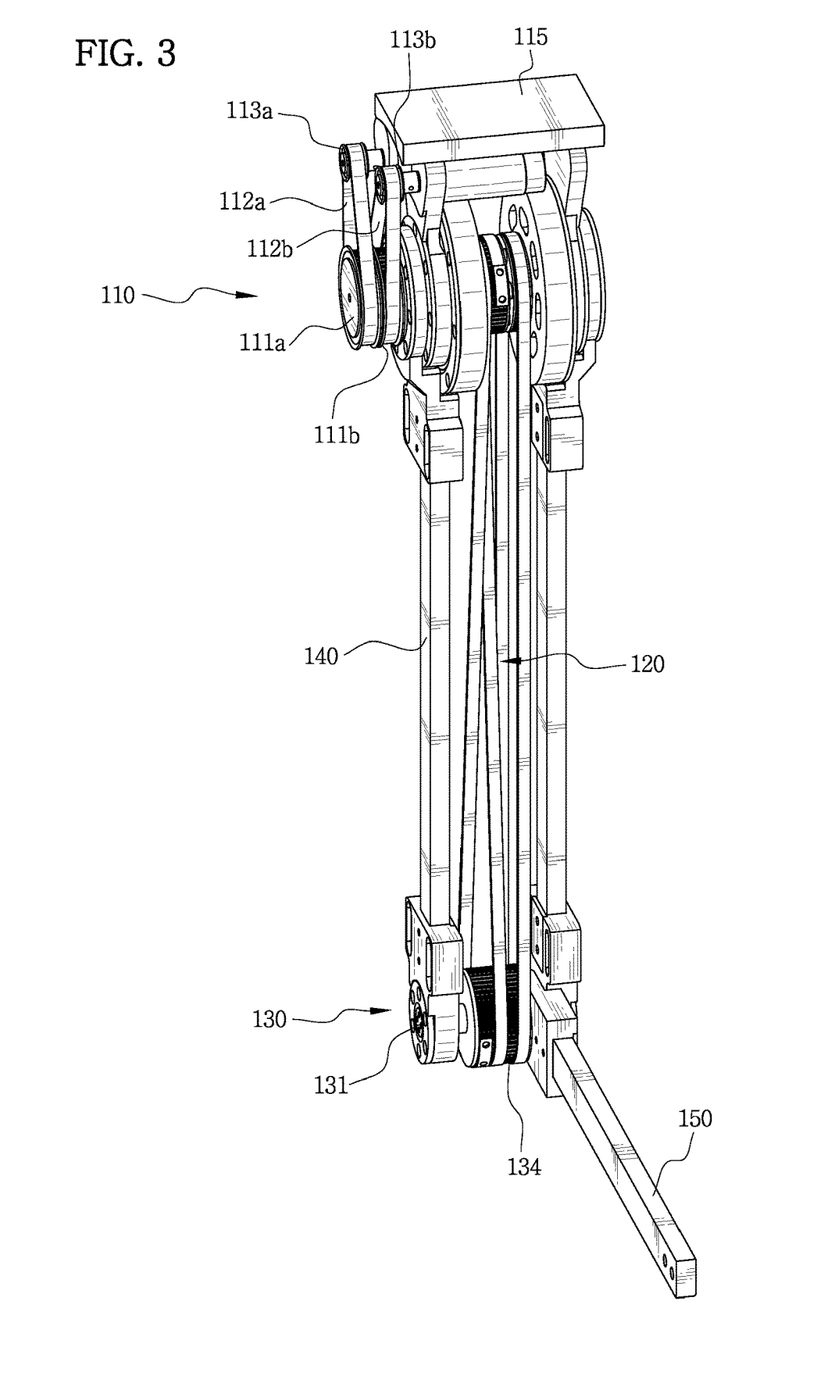
FIG. 3 is a perspective view showing the power transmission apparatus of FIG. 1.
Figure 4:
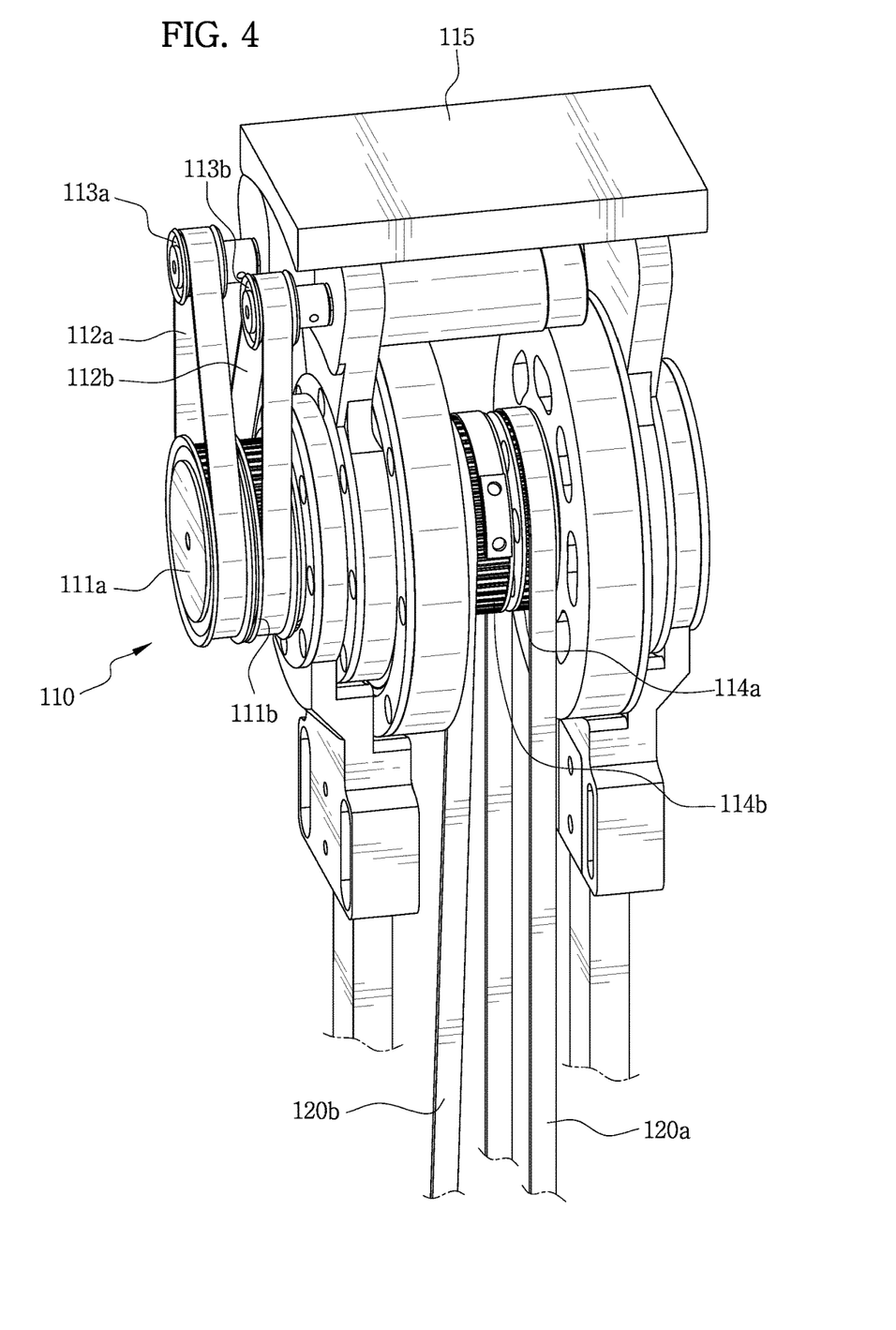
FIG. 4 is a partially enlarged perspective view showing the power transmission apparatus of FIG. 1.
Figure 5:
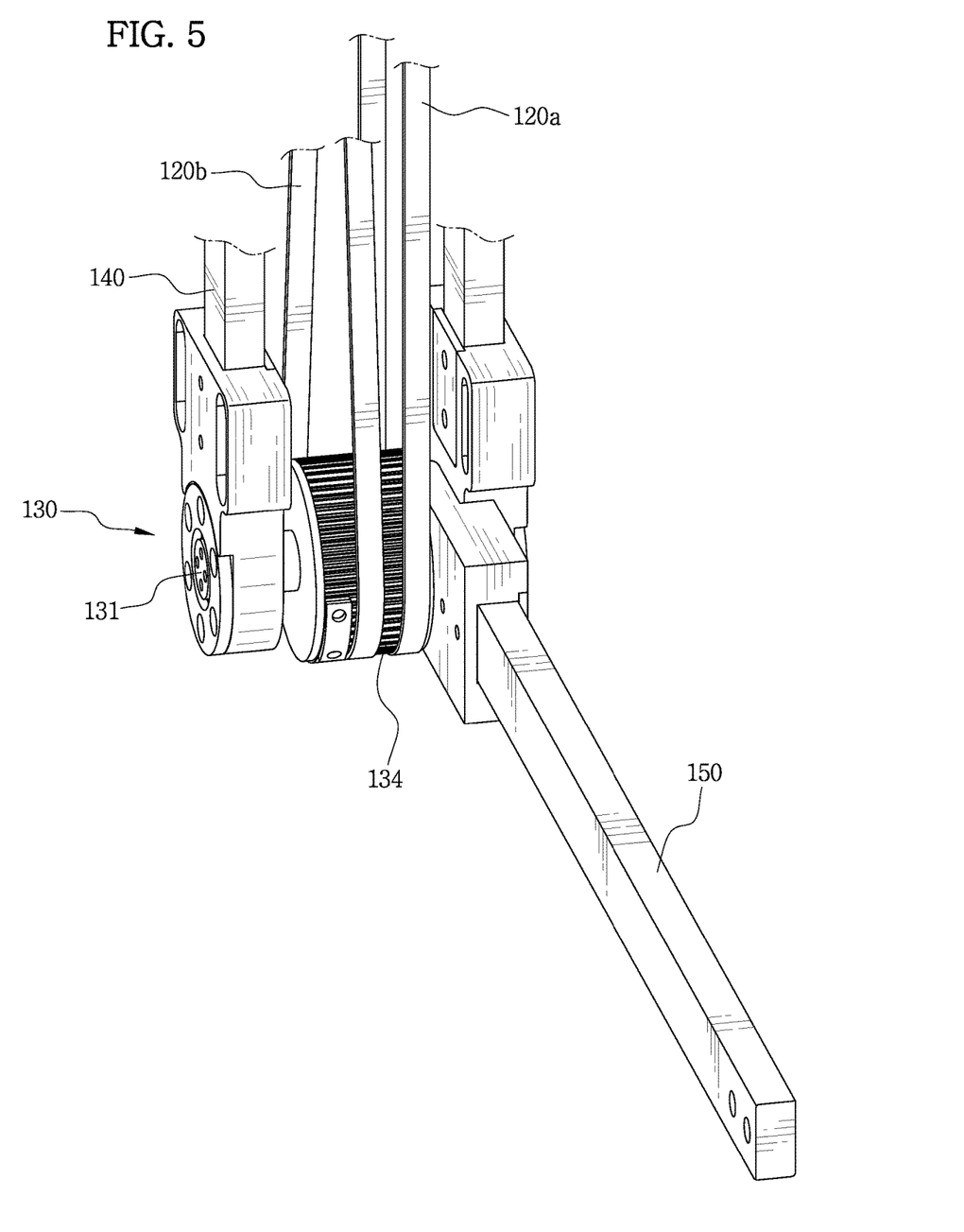
FIG. 5 is a partially enlarged perspective view showing the power transmission apparatus of FIG. 1.
Figure 6:
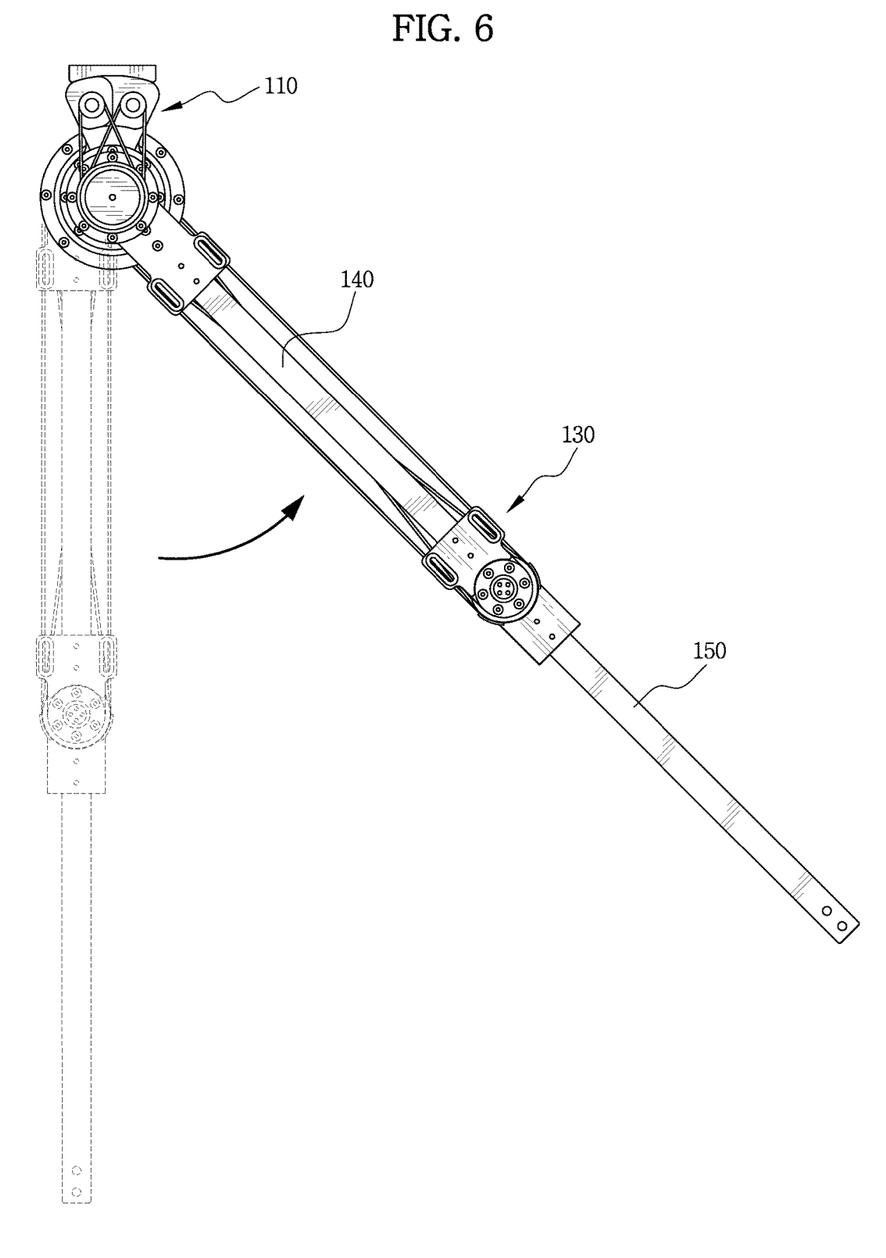
FIG. 6 is a side view showing a usage example of the power transmission apparatus of FIG. 1.

Therefore, as the torque with respect to the driving shafts 111a, 111b is transmitted to the operating shaft 131 by means of the operating belts 120a, 120b, not only the operating belts 120a, 120b and the operating shaft 131 but also the driving link 140 and the operating link 150 rotate with respect to the rotation axes of the driving shafts 111a, 111b, as shown in FIG. 6.

In other words, if the first motor 113a and the second motor 113b rotate in the same direction, the operating link 150 does not rotate with respect to the rotation axis of the operating shaft 131, and the driving link 140 rotates with respect to the rotation axes of the driving shafts 111a, 111b.

Figure 7:
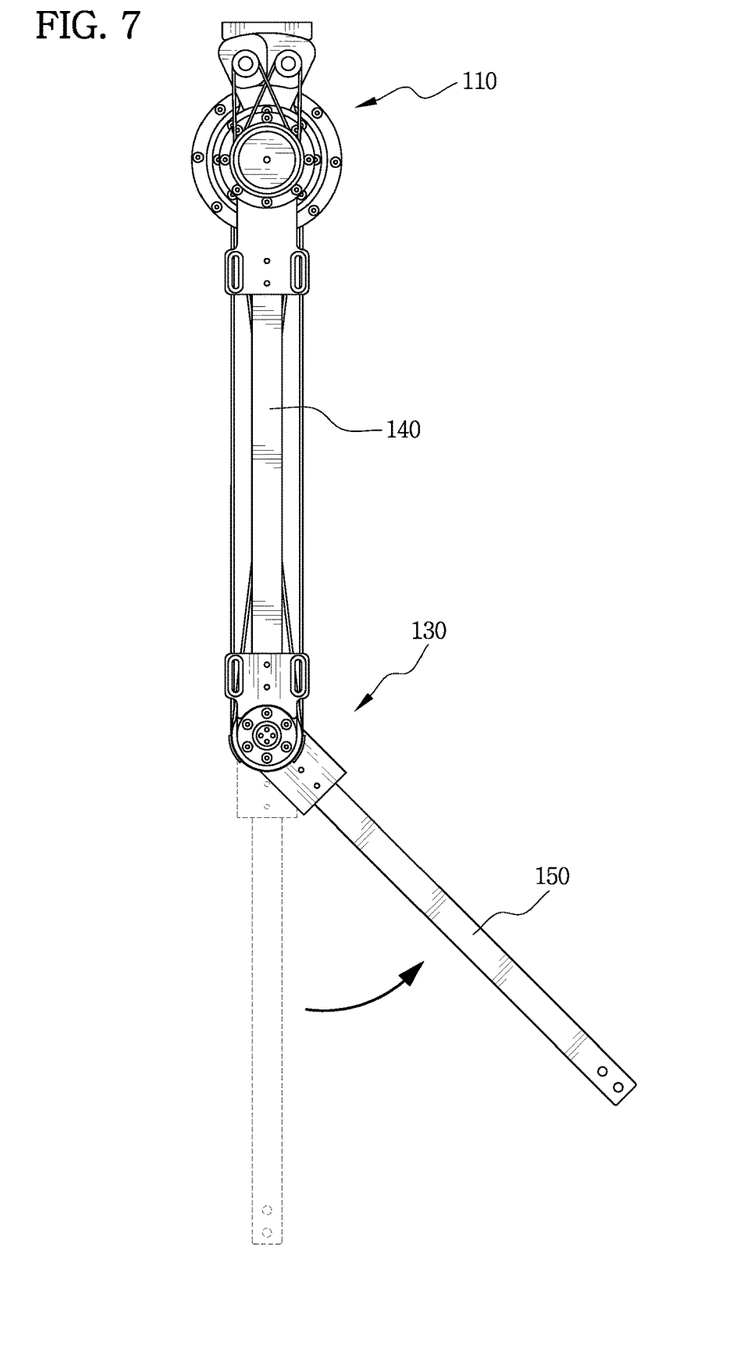
FIG. 7 is a side view showing another usage example of the power transmission apparatus of FIG. 1.

On the contrary, if the first motor 113a and the second motor 113b rotate in opposite directions, the first driving gear 114a and the second driving gear 114b also rotate in opposite directions. Since the rotation directions are changed differently due to the first operating belt 120a and the second operating belt 120b, torques are transmitted to the operating gear 134 in the same direction. Therefore, as shown in FIG. 7, the operating shaft 131 and the operating link 150 rotate with respect to the rotation axis of the operating shaft 131.

Meanwhile, the torques respectively transmitted from the motors 113a, 113b are applied in opposite directions on the first driving shaft 111a and the second driving shaft 111b. Since the first driving shaft 111a and the second driving shaft 111b are disposed on the same straight line and the torques are applied to the first driving gear 114a and the second driving gear 114b in opposite directions, the sum of the torques with respect to the rotation axes of the driving shafts 111a, 111b is 0 (zero), and the driving link 140 does not rotate with respect to the rotation axes of the driving shafts 111a, 111b.

In other words, if the first motor 113a and the second motor 113b rotate in opposite directions, the operating link 150 rotates with respect to the rotation axis of the operating shaft 131, and the driving link 140 does not rotate with respect to the rotation axes of the driving shafts 111a, 111b.

Meanwhile, the features of the links 140, 150 in relation to rotation direction have been explained based on the case where the torques by the first motor 113a and the second motor 113b are identical to each other. However, by controlling rotation speeds and torque directions and intensities of the motors 113a, 113b in various ways, the links 140, 150 may be controlled to make various motions.

A relation between rotation angles q1 and q2 of the first driving gear 114a and the second driving gear 114b and a rotation angle qh of the driving link 140 is as in Equation 1 below.

$$q_h = (q_1 + q_2)/2 \qquad \text{Equation 1}$$

In other words, a rotation angle qh of the thigh with respect to the hip joint of a user is determined according to the sum of a rotation angle q1 of the first driving gear 114a by the first motor 113a and a rotation angle q2 of the second driving gear 114b by the second motor 113b. It should be noted that the intensity of a coefficient in the above equation may vary depending on a ratio of gears respectively connected to the motors 113a, 113b.

A relation between rotation angles q1 and q2 of the first driving gear 114a and the second driving gear 114b and a rotation angle qk of the operating link 150 with respect to the driving link 140 is as in Equation 2 below.

$$q_k = (q_1 - q_2)/2 \qquad \text{Equation 2}$$

In other words, a rotation angle qk of the calf with respect to the knee joint of the user is determined according to a difference between the rotation angle q1 of the first driving gear 114a by the first motor 113a and a rotation angle q2 of the second driving gear 114b by the second motor 113b. In addition, it should be noted that the intensity of a coefficient in the above equation may vary depending on a ratio of gears respectively connected to the motors 113a, 113b.

Based on a demanded posture, demanded rotation angles of the first driving gear 114a and the second driving gear 114b may also be found as a rotation angle qh of the driving link 140 and a rotation angle qk of the operating link 150.

By means of Equations 1 and 2, relations between rotating angular speeds q1' and q2' of the first driving gear 114a and the second driving gear 114b and a rotating angular speed qh' of the driving link 140 and a rotating angular speed qk' of the operating link 150 are as in Equation 3 below.

$$\dot{q}_h = (\dot{q}_1 + \dot{q}_2)/2$$

$$\dot{q}_k = (\dot{q}_1 - \dot{q}_2)/2 \qquad \text{Equation 3}$$

Based on a walking speed and the demanded rotation angles of the first driving gear 114a and the second driving gear 114b obtained as above, rotating angular speeds respectively demanded to the first driving gear 114a and the second driving gear 114b may be obtained.

In addition, relations between the torques T1 and T2 of the first driving gear 114a and the second driving gear 114b and a torque Th of the driving link 140 and a torque Tk of the operating link 150 are as in Equation 4 below.

$$T_1 = (T_h + T_k)/2$$

$$T_2 = (T_h - T_k)/2 \qquad \text{Equation 4}$$

Based on the demanded rotation angles and angular speeds of the first driving gear 114a and the second driving gear 114b obtained as above, torques respectively demanded to the first driving gear 114a and the second driving gear 114b may be obtained.

The torque demanded to the first motor 113a is determined according to the sum of a torque demanded to the driving joint unit 110 and a torque demanded to the operating joint unit 130. In addition, the torque demanded to the second motor 113b is determined according to a difference between a torque demanded to the driving joint unit 110 and a torque demanded to the operating joint unit 130. At this time, coefficients of the above equations may vary to some degrees according to a ratio of gears to which torques of the motors 113a, 113b are transmitted, but their signs are maintained consistently due to the change of direction of the second operating belt 120b.

As described above, based on Equations 1 to 4, rotation speeds and torques demanded to the first motor 113a and the second motor 113b may be obtained. By controlling the first motor 113a and the second motor 113b based on the calculated values, it is possible to assist the user in walking by means of the rotations of the driving link 140 and the operating link 150.

Figure 8:
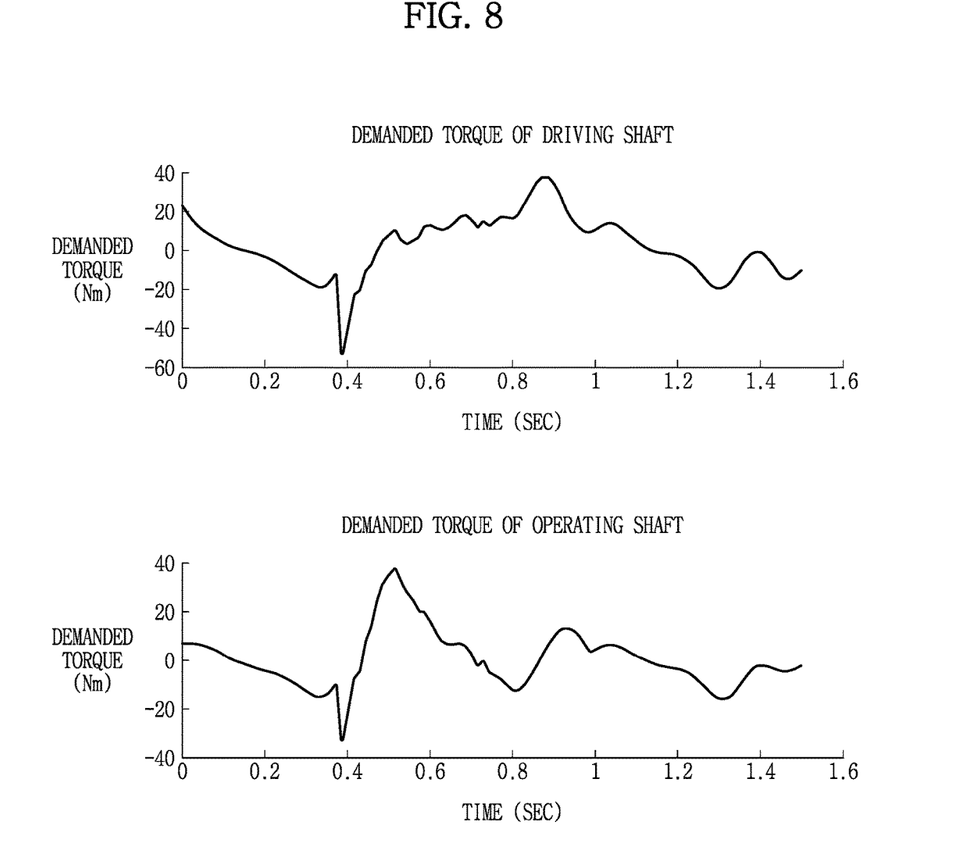
FIG. 8 is a graph showing a torque demanded to a driving joint unit and an operating joint unit according to time when walking.

For reference, a torque demanded to the driving joint unit and a torque demanded to the operating joint unit according to time in walking are depicted in FIG. 8. The intensity of torque demanded on each shaft is about 50 Nm. Therefore, when a motor is individually mounted to each joint unit, each motor should provide a torque of at least 50 Nm.

Figure 9:
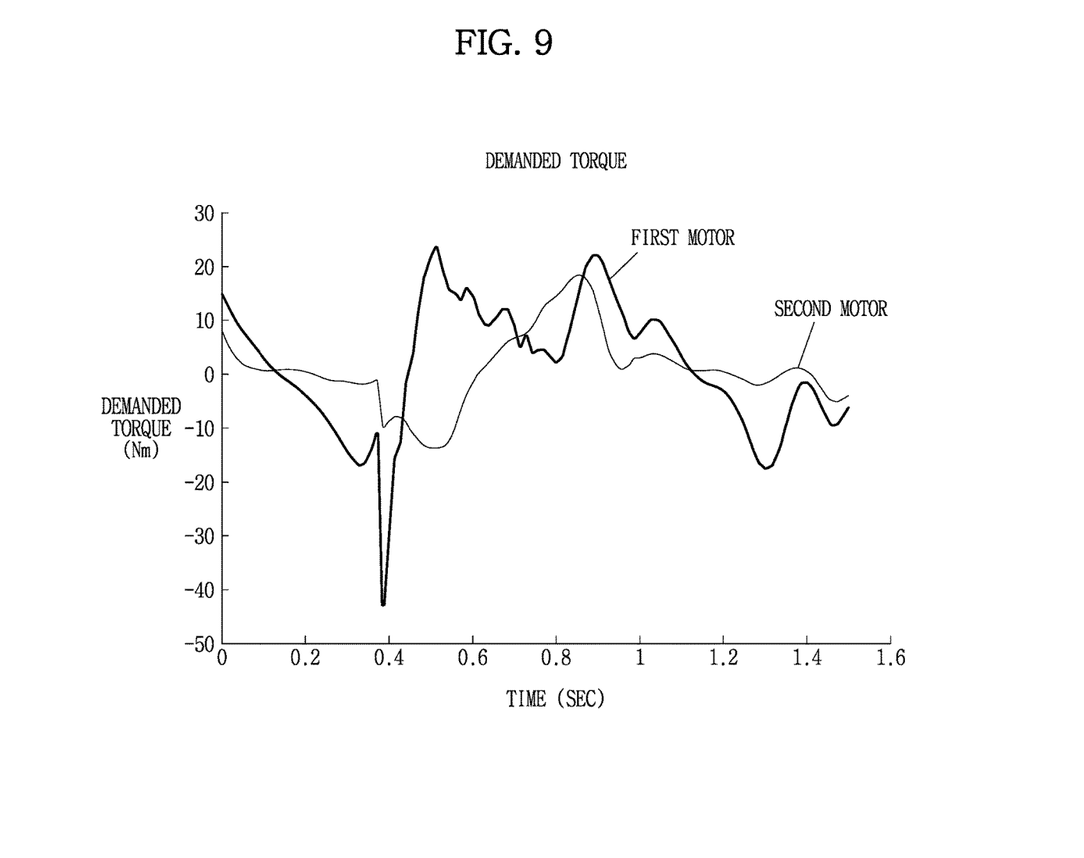
FIG. 9 is a graph showing a torque demanded to first and second driving shaft motors according to time when walking.

Compared to the above, torques T1 and T2 respectively demanded to the motors 113a, 113b according to time in walking are depicted in FIG. 9. Referring to FIG. 9, when the power transmission apparatus 100 according to the present disclosure is used, a torque of 25 Nm or above should be provided to each of the motors 113a, 113b. Therefore, compared with a case where motors are individually mounted to every joint, in this embodiment, motors of a half torque performance may be used. By doing so, the present disclosure has great advantages in energy efficiency and reduction of a product size.

Meanwhile, the first operating belt 120a and the second operating belt 120b may be made of elastic material to serve as a series elastic actuator (SEA) used for an artificial muscle. By doing so, it is possible to absorb inertia generated when the links 140, 150 move or stop, thereby reducing an impact transmitted to the user and assisting in walking in a softer way.

When the operating belts 120a, 120b are made of elastic material, a displacement may occur at the first operating belt 120a and the second operating belt 120b, and thus the degree of freedom of the system increases from 2 degrees of freedom to 4 degrees of freedom. Assuming that a radius of the first driving gear 114a is $r_1$, a radius of the second driving gear 114b is $r_2$, and a radius of the operating gear 134 is $r_3$, a displacement $\Delta l_1$, $\Delta l_2$ of the first operating belt 120a and a displacement $\Delta l_3$, $\Delta l_4$ of the second operating belt 120b are as in Equation 5 below.

$$\Delta l_1 = -r_1 \Delta q_1 + r_1 \Delta q_h + r_3 \Delta q_k$$
$$\Delta l_2 = r_1 \Delta q_1 - r_1 \Delta q_k - r_3 \Delta q_k$$
$$\Delta l_3 = -r_2 \Delta q_2 + r_2 \Delta q_h - r_3 \Delta q_k$$
$$\Delta l_4 = r_2 \Delta q_2 - r_2 \Delta q_h + r_3 \Delta q_k \qquad \text{Equation 5}$$

The degree of freedom of the operating belts 120a, 120b are restricted by a relation of the transmitted torque and a belt spring coefficient, and when a spring coefficient of the first driving belt 112a is k and a spring coefficient of the second driving belt 112b is $l_2$, the restriction condition is as in Equation 6 below.

$$T_1 = r_1 k_1 (\Delta l_2 - \Delta l_1)$$
$$T_2 = r_1 k_2 (\Delta l_4 - \Delta l_3)$$
$$T_k = r_3 k_1 (\Delta l_2 - \Delta l_1) - r_3 k_2 (\Delta l_3 - \Delta l_4)$$

For example, when the first motor 113a and the second motor 113b rotate in the same direction so that the driving link 140 rotates with respect to the rotation axes of the driving shafts 111a, 111b, the torques of the motors 113a, 113b are not instantly transmitted to the driving link 140 but may be slowly transmitted to driving link 140 until the operating belts 120a, 120b are elongated to some degree. Therefore, the thigh of the user is not abruptly moved, but a series of walking motions may be softly connected.

The embodiments of the present disclosure have been described in detail with reference to the accompanying drawings, but the present disclosure is not limited to the embodiments but may be modified in various ways without departing from the scope of the present disclosure. Therefore, the embodiments in the present disclosure are not intended to limit the scope of the present disclosure but intended for illustration, and the scope of the present disclosure is not limited to the embodiments. Therefore, the embodiments described above should be understood as being illustrative in all aspects, rather than restrictive. The scope of the present disclosure to be protected should be interpreted based on the appended claims, and all equivalents thereof should be understood as falling within the scope of the present disclosure.

What is claimed is:

1. A power transmission apparatus, comprising:
    a first driving gear fixed to a first driving shaft;
    a second driving gear fixed to a second driving shaft that is coaxial with the first driving shaft;
    an operating gear fixed to an operating shaft;
    a first operating belt coupling the first driving gear to the operating gear;
    a second operating belt coupling the second driving gear to the operating gear;
    a driving link having a first end rotatably coupled to the first driving shaft or the second driving shaft, and a second end rotatably coupled to the operating shaft; and
    an operating link fixed to the operating shaft.

2. The power transmission apparatus according to claim 1, further comprising:
    an operating joint attached to the operating shaft;
    a first motor configured to transmit torque to the first driving shaft; and
    a second motor configured to transmit torque to the second driving shaft,
    wherein the torque demanded by the first motor is determined according to a sum of a torque demanded by a driving joint unit, which includes the first driving gear and the second driving gear, and a torque demanded by the operating joint, and
    wherein the torque demanded by the second motor is determined according to a difference of the torque demanded by the driving joint unit and the torque demanded by the operating joint.

3. The power transmission apparatus according to claim 2, wherein
    the driving joint unit is configured to be fixed to an upper body of a user,
    the driving link is configured to be fixed to a thigh of the user,
    the operating link is configured to be fixed to a calf of the user, and
    the driving link and the operating link are configured to rotate with respect to each other to assist with walking of the user.

4. The power transmission apparatus according to claim 3, wherein the first motor and the second motor are respectively connected to the first driving shaft and the second driving shaft.

5. The power transmission apparatus according to claim 3, wherein
    the driving shafts are configured to be disposed at a side of a hip joint of the user, and
    the operating shaft is configured to be disposed at a side of a knee joint of the user.

6. The power transmission apparatus according to claim 3, wherein the power transmission apparatus is configured such that a sum of a rotation angle of the first motor and a rotation angle of the second motor determines a rotation angle of the thigh with respect to a hip joint of the user, and a difference of the rotation angle of the first motor and the rotation angle of the second motor determines a rotation angle of the calf with respect to a knee joint of the user.

7. The power transmission apparatus according to claim 1, wherein the second operating belt is connected to the second driving gear and the operating gear in a figure eight shape.

8. The power transmission apparatus according to claim 1, wherein the first operating belt and the second operating belt are made of an elastic material.

9. The power transmission apparatus according to claim 1, further comprising:
    a motor support structure;
    a first motor fixed to the motor support structure;
    a second motor fixed to the motor support structure;
    a first driving belt connecting the first motor to the first driving shaft; and
    a second driving belt connecting the second motor to the second driving shaft.

10. The power transmission apparatus according to claim 1, wherein the driving link is disposed between the first driving shaft and the operating shaft.

11. The power transmission apparatus according to claim 1, wherein the first driving gear is coaxial with the second driving gear.

\* \* \* \* \*